United States Patent [19]

Castro et al.

[11] Patent Number: 5,382,255

[45] Date of Patent: Jan. 17, 1995

[54] APPARATUS AND METHOD FOR ASSEMBLY OF SURGICAL INSTRUMENTS

[75] Inventors: Salvatore Castro, Seymour; Paul J. Phillips, Middlebury; Giovanni Gonzalez, Norwalk, all of Conn.

[73] Assignee: United States Surgical Corporation, Norwalk, Conn.

[21] Appl. No.: 2,208

[22] Filed: Jan. 8, 1993

[51] Int. Cl.⁶ .............................................. A61B 17/10
[52] U.S. Cl. .................................... 606/143; 227/901; 403/315; 606/139
[58] Field of Search .................. 606/139, 142, 143; 227/175, 181, 901; 403/315, 316, 348, 350

[56] References Cited

U.S. PATENT DOCUMENTS

| | | |
|---|---|---|
| D. 276,650 | 12/1984 | Green et al. . |
| 2,008,367 | 7/1935 | Rhinevault . |
| 2,092,060 | 9/1937 | Gairing ............................. 403/348 |
| 2,741,248 | 4/1956 | Woodhall . |
| 2,968,041 | 1/1961 | Skold . |
| 3,585,985 | 6/1971 | Gould . |
| 3,596,944 | 8/1971 | Ecker et al. .................... 403/348 |
| 3,603,310 | 9/1971 | Mottin et al. . |
| 3,631,707 | 1/1972 | Miller . |
| 3,777,538 | 12/1973 | Weatherly et al. . |
| 3,834,392 | 9/1974 | Lampman et al. . |
| 3,848,773 | 11/1974 | Adler et al. . |
| 3,856,016 | 12/1974 | Davis . |
| 3,870,048 | 3/1975 | Yoon . |
| 3,882,854 | 5/1975 | Hulka et al. . |
| 3,954,108 | 5/1976 | Davis . |
| 3,955,581 | 5/1976 | Spasiano et al. . |
| 3,989,049 | 11/1976 | Yoon . |
| 4,027,510 | 6/1977 | Hiltebrandt . |
| 4,038,987 | 8/1977 | Komiya . |
| 4,064,881 | 12/1977 | Meredith . |
| 4,084,594 | 4/1978 | Mosior . |
| 4,085,743 | 4/1978 | Yoon . |
| 4,101,063 | 7/1978 | Kapitanov et al. . |
| 4,103,680 | 8/1978 | Yoon . |
| 4,152,920 | 5/1979 | Green . |
| 4,166,466 | 9/1979 | Jarvik . |
| 4,169,476 | 10/1979 | Hiltebrandt . |
| 4,185,762 | 1/1980 | Froehlich . |
| 4,188,953 | 2/1980 | Klieman et al. . |
| 4,196,836 | 4/1980 | Becht . |
| 4,226,239 | 10/1980 | Polk et al. . |
| 4,226,242 | 10/1980 | Jarvik . |
| 4,228,895 | 10/1980 | Larkin . |
| 4,230,116 | 10/1980 | Watson . |
| 4,240,411 | 12/1980 | Hosono . |
| 4,242,902 | 1/1981 | Green . |
| 4,246,903 | 1/1981 | Larkin . |
| 4,257,419 | 3/1981 | Göltner et al. . |
| 4,273,129 | 6/1981 | Boebel . |
| 4,296,751 | 10/1981 | Blake, III et al. . |
| 4,299,224 | 11/1981 | Noiles . |
| 4,316,468 | 2/1982 | Klieman et al. . |

(List continued on next page.)

FOREIGN PATENT DOCUMENTS

| | | |
|---|---|---|
| 0406724 | 1/1991 | European Pat. Off. . |
| 0409569 | 1/1991 | European Pat. Off. . |
| 2330182 | 1/1975 | Germany . |
| 2546696 | 10/1975 | Germany . |
| 3802651 | 8/1989 | Germany . |
| 1093329 | 5/1984 | U.S.S.R. . |
| 8910094 | 11/1989 | WIPO . |
| 9003763 | 4/1990 | WIPO . |

OTHER PUBLICATIONS

Richard Wolf Instruction Manual, "Laparoscopic Sterilization with Spring Clips," by Jaroslav F. Hulka, M. D. Information Booklet for Auto Suture ® Premium Surgiclip ™ Titanium Disposable Automatic Clip Appliers.

(List continued on next page.)

*Primary Examiner*—Tamara L. Graysay

[57] ABSTRACT

The present invention relates to surgical instruments having a housing or elongated cartridge, a frame and an apparatus for releasably connecting the housing to the frame. Typically, the housing has active elements which perform a particular function during a surgical procedure, such as forceps, graspers, clip appliers or staplers. The frame includes an actuating system for actuating the active elements, such as a pivotal handle or a release lever.

19 Claims, 9 Drawing Sheets

U.S. PATENT DOCUMENTS

| | | |
|---|---|---|
| 4,325,376 | 4/1982 | Klieman et al. |
| 4,325,377 | 4/1982 | Boebel . |
| 4,335,928 | 6/1982 | Barrett et al. . |
| 4,338,947 | 7/1982 | Williams . |
| 4,367,746 | 1/1983 | Derechinsky . |
| 4,372,316 | 2/1983 | Blake, III et al. . |
| 4,374,523 | 2/1983 | Yoon . |
| 4,393,883 | 7/1983 | Smyth et al. . |
| 4,412,539 | 11/1983 | Jarvik . |
| 4,425,915 | 1/1984 | Ivanov . |
| 4,430,997 | 2/1984 | DiGiovanni et al. . |
| 4,440,170 | 4/1984 | Golden et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,479,489 | 10/1984 | Tucci . |
| 4,480,641 | 11/1984 | Failla et al. . |
| 4,481,952 | 11/1984 | Pawelec . |
| 4,492,232 | 1/1985 | Green . |
| 4,505,414 | 3/1985 | Filipi . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,550,715 | 11/1985 | Santangelo et al. . |
| 4,557,263 | 12/1985 | Green . |
| 4,558,706 | 12/1985 | Nakada et al. . |
| 4,562,839 | 1/1986 | Blake, III et al. . |
| 4,572,183 | 2/1986 | Juska . |
| 4,576,166 | 3/1986 | Montgomery et al. . |
| 4,589,421 | 5/1986 | Ullman . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,633,882 | 1/1987 | Matsuo et al. . |
| 4,646,740 | 3/1987 | Peters et al. . |
| 4,649,904 | 3/1987 | Krauter et al. . |
| 4,662,373 | 5/1987 | Montgomery et al. . |
| 4,662,374 | 5/1987 | Blake, III . |
| 4,674,501 | 6/1987 | Greenburg . |
| 4,674,504 | 6/1987 | Klieman et al. . |
| 4,682,491 | 7/1987 | Pickard . |
| 4,691,853 | 9/1987 | Storace . |
| 4,694,544 | 9/1987 | Chapman .............. 403/316 |
| 4,700,694 | 10/1987 | Shishido . |
| 4,712,549 | 12/1987 | Peters et al. . |
| 4,759,364 | 7/1988 | Boebel . |
| 4,784,137 | 11/1988 | Kulik et al. . |
| 4,841,888 | 6/1989 | Mills et al. . |
| 4,850,350 | 7/1989 | Jackson . |
| 4,850,355 | 7/1989 | Brooks et al. . |
| 4,858,608 | 8/1989 | McQuilkin . |
| 4,874,364 | 10/1989 | Morris et al. . |
| 4,900,307 | 2/1990 | Kulli . |
| 4,919,152 | 4/1990 | Ger . |
| 4,935,010 | 6/1990 | Cox et al. . |
| 4,944,443 | 7/1990 | Oddsen et al. . |
| 5,026,379 | 6/1991 | Yoon . |
| 5,030,226 | 7/1991 | Green et al. . |
| 5,040,715 | 8/1991 | Green et al. . |
| 5,049,152 | 9/1991 | Simon et al. . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,171,247 | 12/1992 | Hughett et al. . |
| 5,171,249 | 12/1992 | Stefanchik et al. . |

OTHER PUBLICATIONS

Information Booklet for Auto Suture ® Skin and Fascia Surgical Stapling Instruments and Disposable Loading Units.

"Information About Dimethyl Silicone Compounds," Dow Corning, 1988.

"Laparoscopic Sterilization with Electrocautery, Spring-Loaded Clips, and Silastic Bands: Technical Problems and Early Complications," Fertility and Sterility, vol. 27, No. 3, Mar. 1976.

"A Clip Applicator for Laparoscopic Sterilization," Fertility and Sterility, vol. 27, No. 9, Sep. 1976.

"Laparoscopic Sterilization with Spring-Loaded Clips: Double-Puncture Technique," The Journal of Reproductive Medicine, vol. 18, No. 5, May 1977.

"Laparoscopic Sterilization with the Spring Clip: Instrumentation development and Current Clinical Experience," American Journal of Obstetrics and Gynecology, vol. 135, No. 8, Dec. 15, 1979.

Karl Storz Endoscopy-America Promotional Advertisement, "It's Your Choice for Tubal Sterilization," 1981.

"An Applicator for the Hulka Fallopian Tube Clip," American Journal of Obstetrics and Gynecology, vol. 139, No. 6, Mar. 15, 1981.

"Metal Clip Techniques Utilizing Pistol Grip Appliers," The American Journal of Surgery, Feb. 1982.

"Results of Experimental Endoscopic Esophagel Varix Ligation," The American Surgeon, Jan. 1988.

Edward Weck & Company Promotional Advertisement, "We've Corrected Everybody's Flaws," Sep. 1986.

APPARATUS AND METHOD FOR ASSEMBLY OF SURGICAL INSTRUMENTS

BACKGROUND OF THE INVENTION

1. Field of the Invention

The present invention relates to an apparatus and method for the assembly of surgical instruments, especially endoscopic or laparoscopic surgical instruments. More particularly, the invention relates to the assembly of a cartridge assembly to a handle assembly.

2. Background of the Related Prior Art

When manufacturing surgical instruments it is often necessary to connect a handle assembly to active elements which assist the surgeon in performing a particular task during a surgical procedure. Examples of these active elements include forceps, retractors, staplers, clip appliers and the like.

Typically, these active elements are either completely enclosed or partially enclosed within a housing (or cartridge). The housing may be relatively short in length and used during conventional invasive surgical procedures or the housing may be elongated and adapted for use during endoscopic or laparoscopic surgical procedures.

In laparoscopic procedures surgery is performed in the interior of the abdomen through a small incision. In endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated.

Heretofore, when manufacturing the above-mentioned surgical instruments, the housing is typically connected to the handle assembly by manually opening or separating a portion of the handle assembly, inserting a portion of the housing into the handle assembly and resealing the handle assembly. As a result of the manual separating and resealing of the handle assembly, the assembly time, costs and defect rate associated with the production of these types of surgical instruments are relatively high.

Therefore, a need exists for an apparatus which increases the efficiency of the manufacturing process for producing surgical instruments by decreasing the assembly time, defect rate and, ultimately, costs associated with producing the instruments.

SUMMARY OF THE INVENTION

The present invention relates to a surgical instrument which comprises housing means and active element means for performing a function during surgical procedures, frame means having element actuating means for actuating the active element means and receiving means for reception of at least a portion of the housing means, and means for releasably connecting the housing means to the frame means such that the active element means is operatively connected to the element actuating means. Preferably, the connecting means comprises a locking member adaptable for positioning about the housing means adjacent the frame means, the locking member includes at least one locking tab spatially positioned at a proximal end thereof which engages with a corresponding locking channel positioned adjacent the receiving means.

Generally, the housing means includes an array of surgical fasteners, such as clips. The active element means includes jaw means positioned at a distal end of the housing, means for individually advancing the surgical fasteners into a position within the jaw means, and means for closing said jaw means. The frame means includes fastener advancing actuating means for actuating the fastener advancing means and jaw closing actuating means for actuating the jaw closing means.

In an alternate embodiment, an apparatus for releasably connecting endoscopic means to handle means is provided such that at least a portion of the endoscopic means is removably maintained within the handle means and active elements within the endoscopic means are operatively connected to the handle means. The apparatus comprises a locking member rotatably, slidably positioned adjacent a proximal end of the endoscopic means, and includes at least one locking tab positioned at a proximal end portion of the locking member which engages a corresponding locking channel positioned adjacent a distal end portion of the handle means.

The present invention also relates to a method for manufacturing surgical instruments which comprises inserting at least a portion of a proximal end of an endoscopic housing into a corresponding opening having at least one keyway positioned at least partially around the perimeter of the opening at a distal end of a handle assembly, positioning connecting means having at least one tab positioned at proximal end thereof adjacent the proximal end of the housing, positioning the at least one tab into engagement with the at least one keyway and rotating the connecting means such that the proximal end portion of the housing is releasably, rotatably maintained within the handle assembly.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

The preferred embodiment of the present invention will be described with reference to surgical clip appliers whose structure and function are described in, commonly assigned, U.S. Pat. Nos. 5,084,057 and 5,100,420 to Green et. al. both of which are incorporated herein by reference. Though, it should be noted that the present invention is adaptable for use in various surgical instrument having a handle assembly connected to a housing or cartridge. The exemplary clip appliers described herein are substantially identical, therefore like elements will have the same reference numerals.

Figure 1:
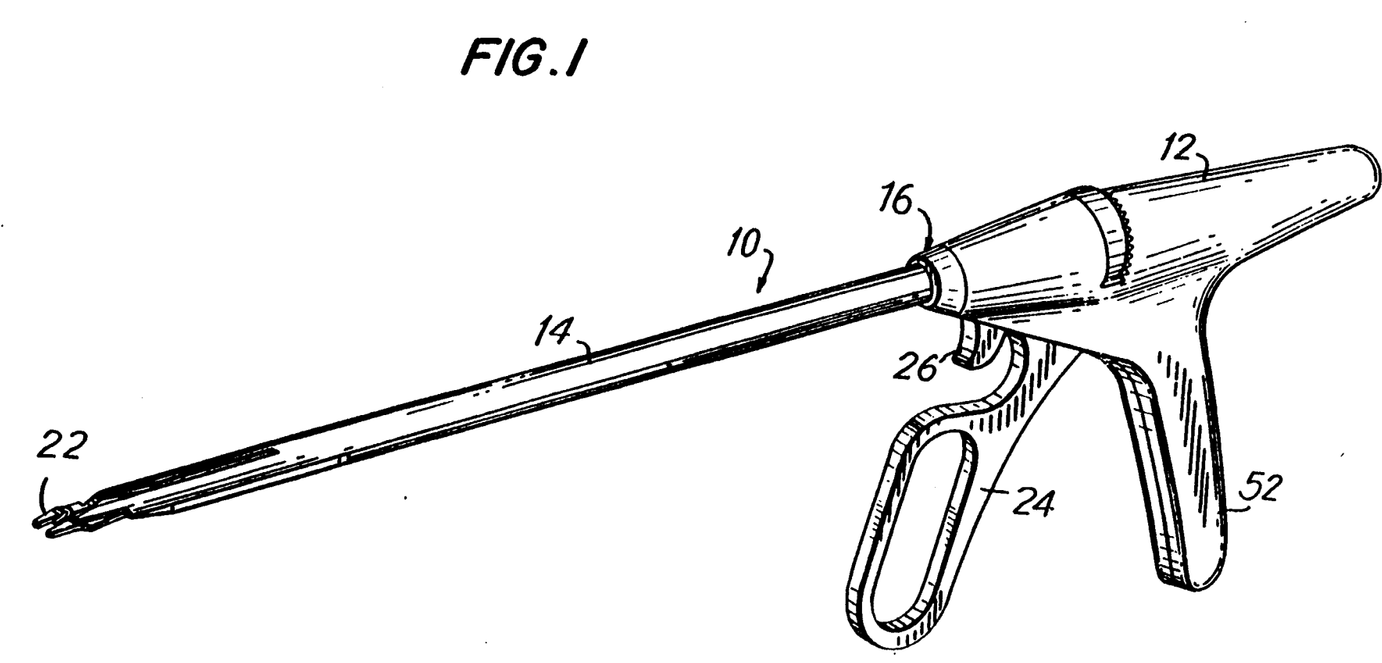
FIG. 1 is a perspective view of a surgical clip applier having a cartridge assembly attached to a handle assembly with the connecting member of the present invention.

Referring to FIG. 1, one embodiment in which a cartridge or housing is secured to a handle assembly is shown. The surgical clip applier 10 shown includes pistol grip handle section or frame 12 and housing or endoscopic sector 14 similar to the clip applier described in U.S. Pat. No. 5,084,057 mentioned above. The connecting member 16 of the present invention is provided to engage a corresponding opening in handle section 12 and maintain at least a portion of the proximal end of housing 14 within handle section 12.

Figure 2:
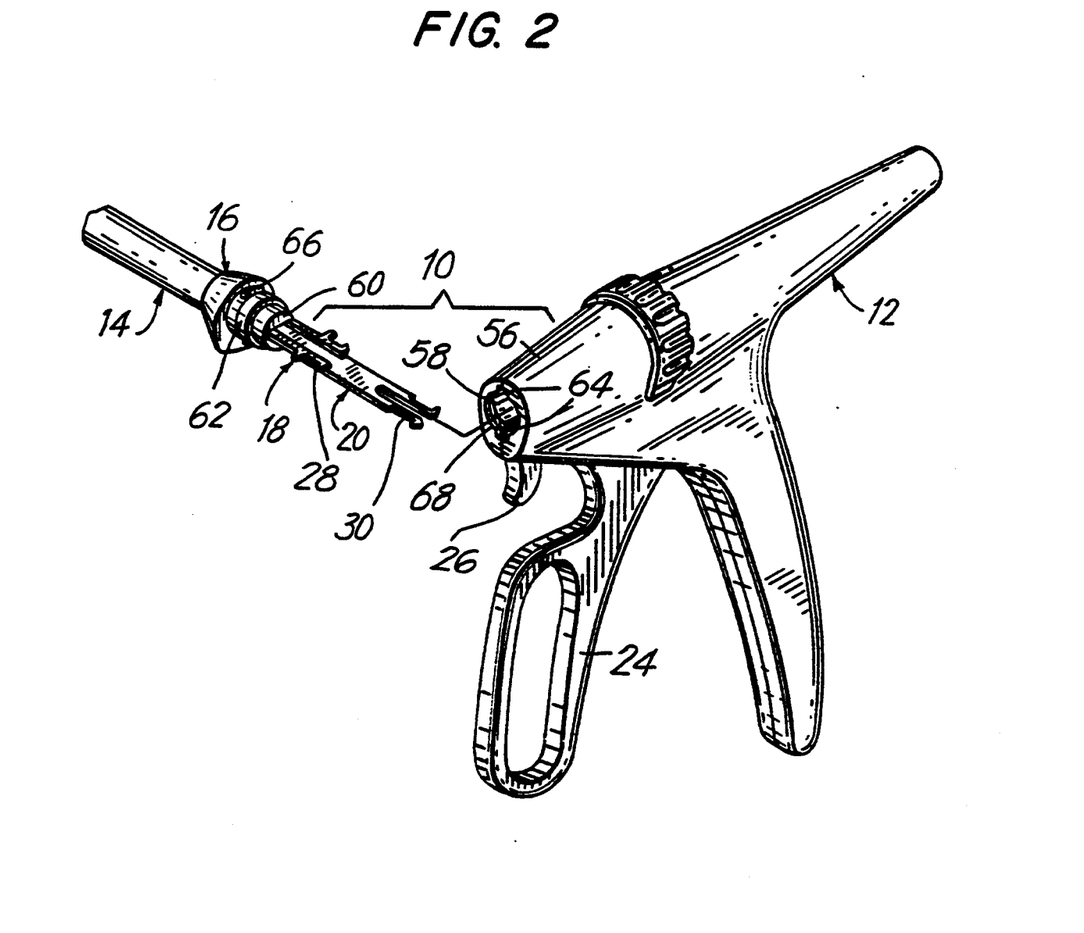
FIG. 2 is a perspective view with parts separated of a portion of the surgical clip applier of FIG. 1, illustrating the interconnection between a cartridge assembly, a pistol grip handle assembly and the connecting member of the present invention.

Referring now to FIG. 2, housing 14 includes the same structure and functions in the same manner as the endoscopic section of the apparatus described in U.S. Pat. Nos. 5,084,057 and 5,100,420 previously mentioned. Included in this exemplary housing is crimping channel 18 and clip pusher 20. Crimping channel 18 is provided to close a pair of flexible opposing jaws 22, shown in FIG. 1, positioned at the distal end of housing 14, while clip pusher 20 is provided to individually advance surgical clips between the jaws. As described in the above mentioned patents, the surgical clips are advanced from a longitudinal array of clips.

Figure 3:
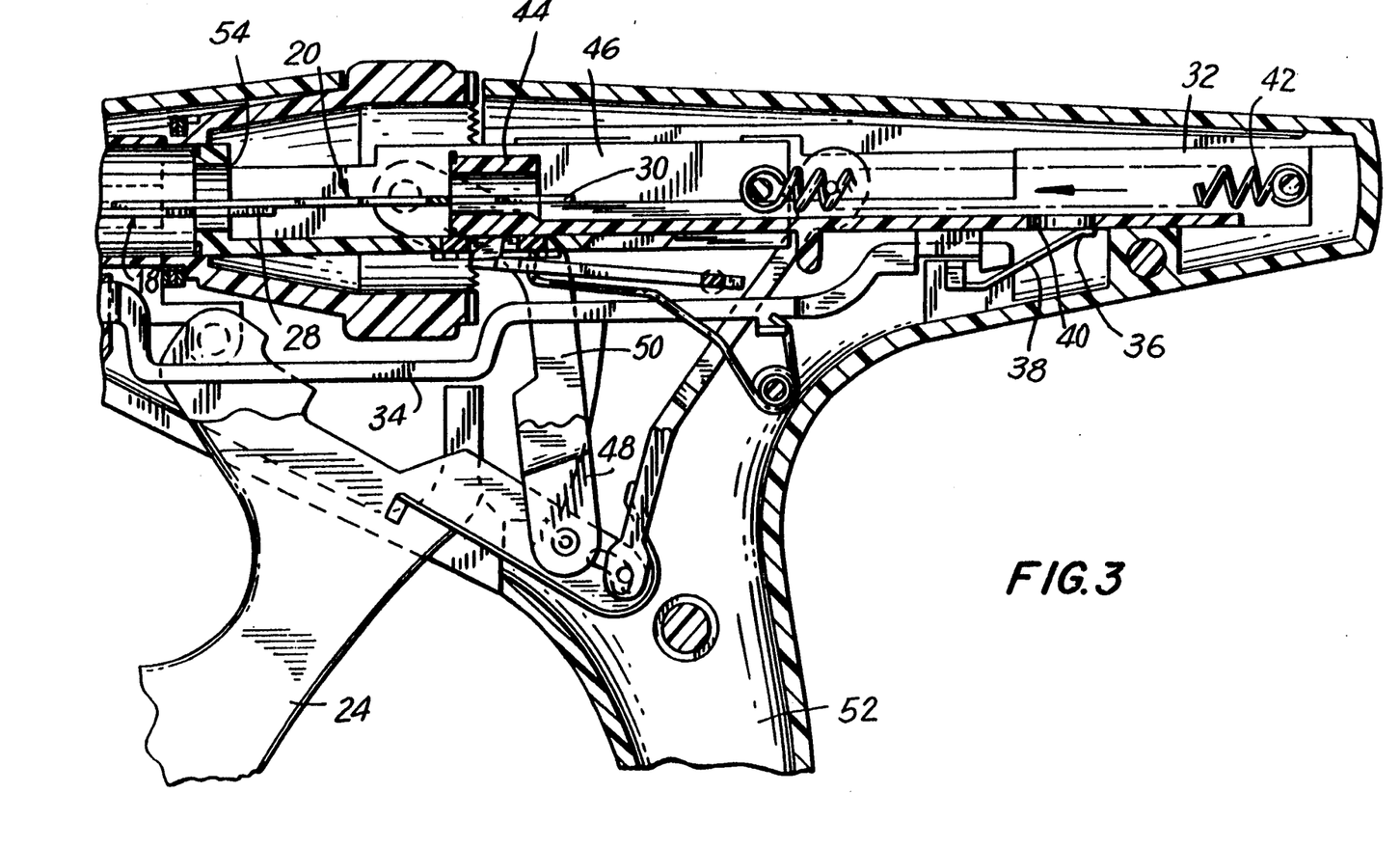
FIG. 3 is a cross-sectional view of a portion of the handle section of FIG. 1, illustrating the operative connections between the cartridge assembly and the handle section.
Figure 4:
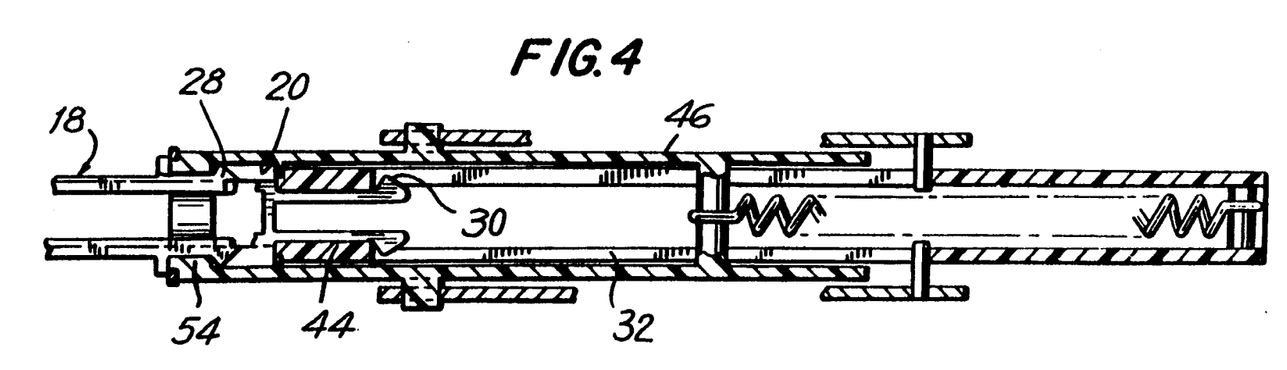
FIG. 4 is a cross-sectional view from above of the operative connections between the cartridge assembly and the handle assembly of FIG. 3.

Handle section 12 includes element actuating members such as handle 24 and trigger 26 which are operatively connected to the active elements within housing 14, namely the proximal end portion 28 of crimping channel 18 and the proximal end portion 30 of clip pusher 20, respectively. As shown in FIGS. 3 and 4, the proximal end portion 30 of clip pusher 20 is operatively connected to trigger 26 via pusher tube 32 (i.e., the first transmission system) and pusher release lever 34. Thus, when trigger 26 is proximally advanced toward the handle, pusher release lever 34 causes catch 36 of pusher leaf spring 38 to disengage from aperture 40 of pusher tube 32 thereby releasing pusher tube 32. The fastener advancing mechanism according to the present invention includes, trigger 26, release lever 34, catch 36 and leaf spring 38. When released, pusher tube 32 moves distally, under the action of mainspring 42, causing clip pusher 20 to advance the next clip in the clip array between the jaws. As shown in FIG. 4, the proximal end portion 30 of clip pusher 20 is configured to engage distal opening 44 in pusher tube 32 and remain rotatably maintained therein. Similarly, the proximal end portion 28 of crimping channel 18 is operatively connected to handle 24 via channel tube 46 (i.e., the second transmission system) and channel links 48 and 50. Thus, when handle 24 is proximally advanced toward instrument body or hand grip 52 of handle section 12, channel links 48 and 50 cause channel tube 46 and crimping channel 18 to move distally. Distal motion of crimping channel 18 causes the jaws of housing 14 to close. As shown in FIG. 4, the proximal end portion 28 of crimping channel 18 is configured to engage distal opening 54 in channel tube 46 and remains rotatably maintained therein. The operative connections of housing 14 to handle section 12 are further described in U.S. Pat. No. 5,084,057 mentioned above.

Referring again to FIG. 2, the distal end portion 56 of handle section 12 is provided with opening 58 to receive crimping channel 18, clip pusher 20, the proximal end portion 60 of housing 14 and collar 62 of connecting member 16. This configuration removes the need to separate the handle section to allow insertion of the proximal portion of housing 14, which, as noted above, is commonly performed within the prior art. Keyways 64 are spatially positioned on the perimeter of opening 58, as shown, and are provided to receive tabs 66 positioned at the proximal end portion of connecting member 16 so as to facilitate the connection of housing 14 to handle section 12.

In operation, connecting member 16 is initially positioned at the proximal end of housing 14, distal to collar 62. The proximal end portion 60 of housing 14 is then inserted into opening 58 so that crimping channel 18 operatively connects to handle 24 and clip pusher 20 operatively connects to trigger 26, as described above. In addition to being operatively connected to handle 24 and trigger 26, the proximal end portion 28 of crimping channel 18 and the proximal end portion 30 of clip pusher 20 are, preferably, arranged within handle section 12 so as not to inhibit or limit rotational movement of housing 14 with respect to handle section 12.

Figures 5, 6:
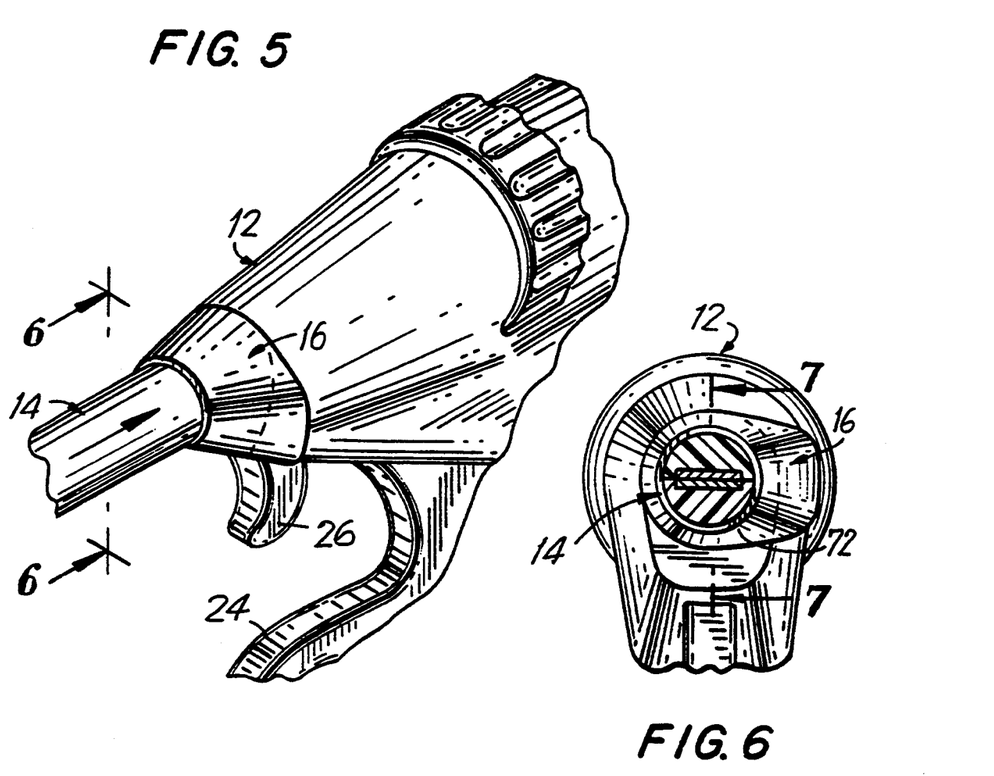
FIG. 5 is a perspective view of a portion of the instrument of FIG. 1, illustrating the connecting member in the attaching position.
FIG. 6 is a partial cross-sectional view of the instrument of FIG. 1, taken along line 6—6 of FIG. 5.
Figure 7:
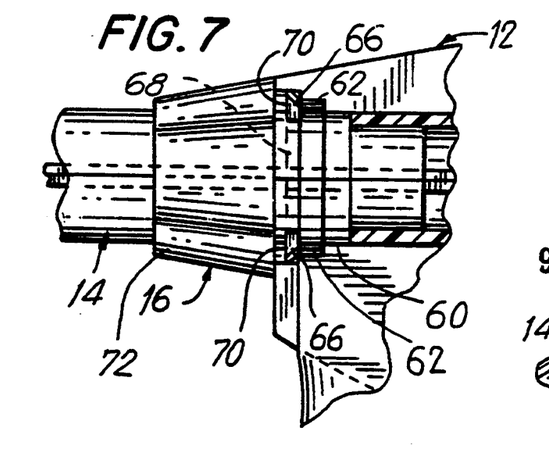
FIG. 7 is a partial cross-sectional view taken along line 7—7 of FIG. 6, illustrating the locking connection between the connecting member and the handle assembly.

Once housing 14 is positioned within handle section 12 to the point where collar 62 of connecting member 16 is received within opening 58, tabs 66 of connecting member 16 are aligned with keyways 64 and moved proximally to slide through keyways 64 into engagement with channel 68 of handle section 12, as shown in FIGS. 5-7.

Referring now to FIGS. 8-11, connecting member 16 is rotated so that tabs 66 create a friction fit with the interior surface 70 of channel 68, thereby locking (or coupling) connecting member 16 to handle section 12. When the connecting member is locked to handle section 12 as described above, collar 62 is maintained within handle section 12, thus securing housing 14 to handle section 12. In addition, the forces exerted on collar 62 when closing the jaws in housing 14, are transferred and distributed to handle section 12 through connecting member 16.

Figure 8:
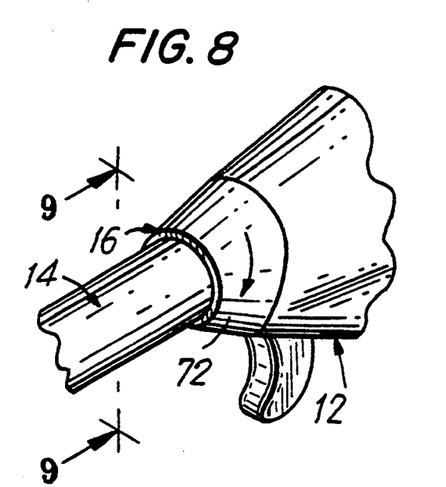
FIG. 8 is a perspective view of a portion of the instrument of FIG. 1, illustrating the connecting member in a locked position.
Figure 9:
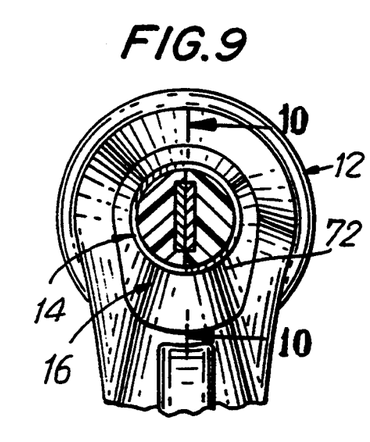
FIG. 9 is a partial cross-sectional view of the instrument of FIG. 1, taken along line 9—9 of FIG. 8 and illustrating the locked connecting member conforming to the ornamental features of the handle assembly.
Figure 10:
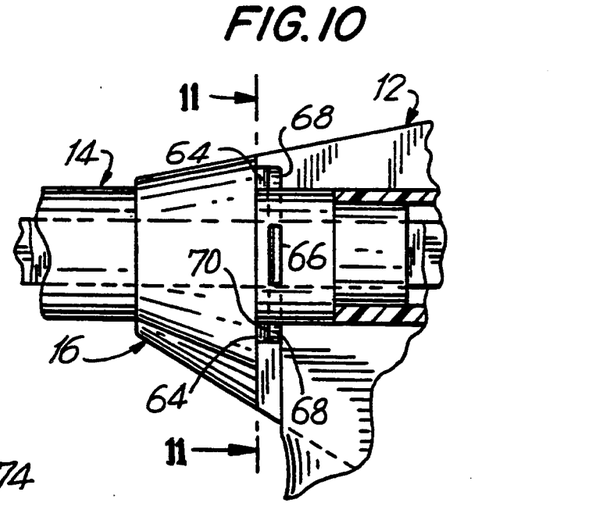
FIG. 10 is a partial cross-sectional view of the instrument of FIG. 1, taken along line 10—10 of FIG. 9 and illustrating the tab displaced from the keyway approximately 90°.
Figure 11:
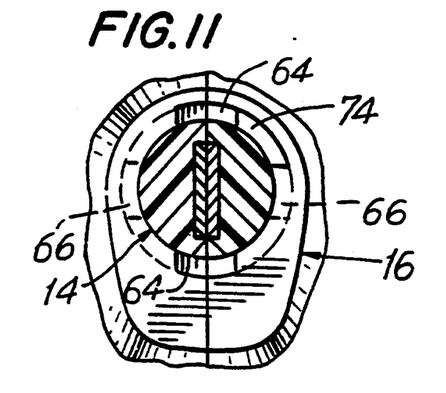
FIG. 11 is a partial cross-sectional view of the instrument of FIG. 1, taken along line 11—11 of FIG. 10 and illustrating a blocking member which limits the rotational movement of the connecting member.

Preferably, tabs 66 are positioned on connecting member 16 in such a manner that when connecting member 16 is rotated 90° nose 72 of connecting member 16 conforms with the ornamental features of handle section 12, as shown in FIGS. 8 and 9. As a result, tabs 66 will be displaced from keyways 64 approximately 90°, as shown in FIG. 10. Blocking member 74 may also be positioned within channel 68 to limit rotational movement of tabs 66 a predetermined number of degrees, preferably 90° as shown in FIG. 11, so as to ensure that the nose conforms with the ornamental features of handle section 12.

Figure 12:
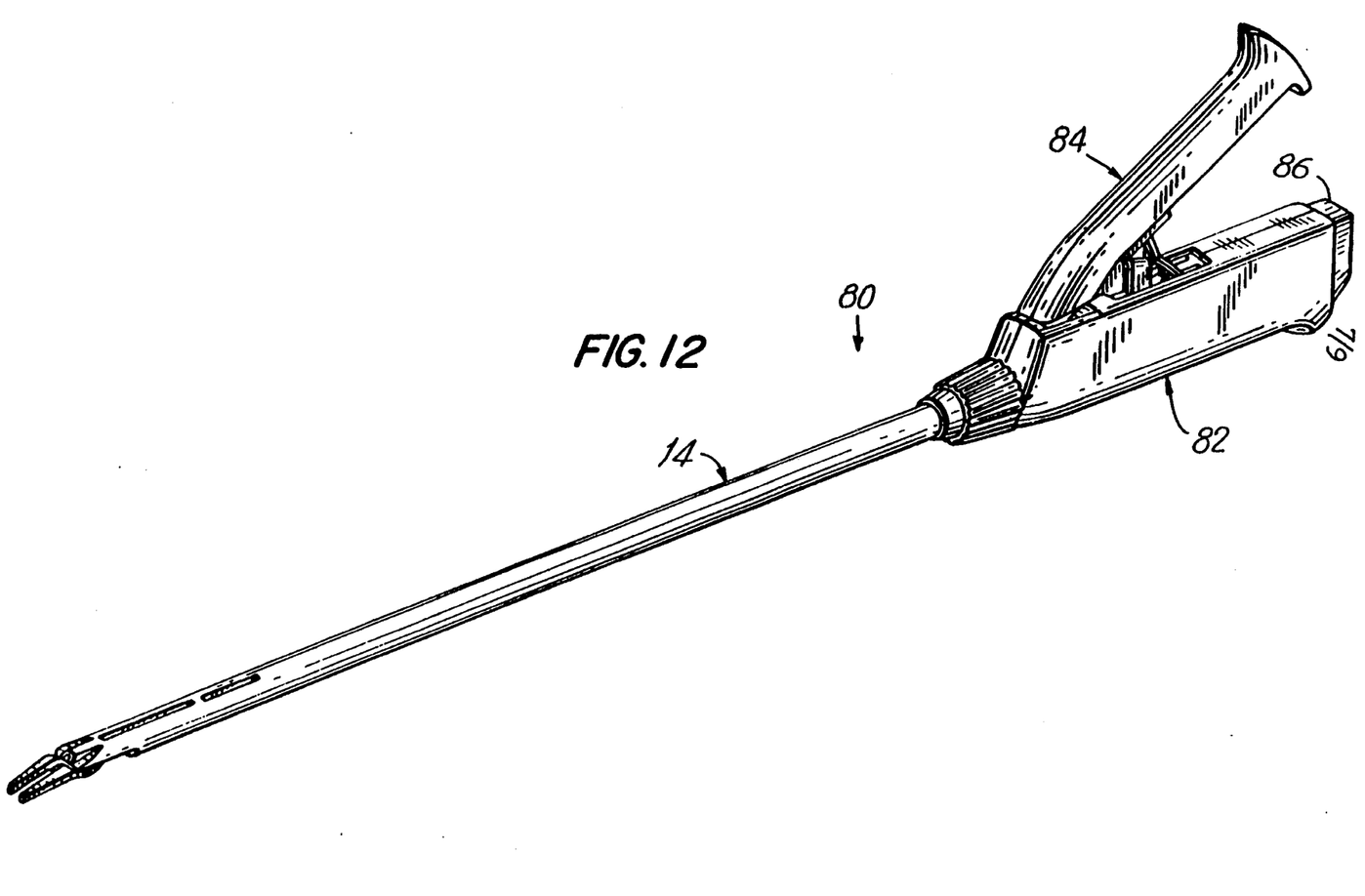
FIG. 12 is a perspective view of a surgical clip applier having a cartridge assembly connected to a palm grip handle assembly.

Referring now to FIG. 12, another embodiment in which a cartridge or housing is secured to a handle assembly is shown. The surgical clip applier 80 shown has a palm grip handle section 82 and a housing 14 similar to that described in U.S. Pat. No. 5,100,420 mentioned above. Similar to the above mentioned embodiment, handle section 82 includes handle 84 and release button 86 which are operatively connected to the active elements within housing 14, namely, the proximal end portion 28 of crimping channel 18 and the proximal end portion 30 of clip pusher 20, respectively.

Figure 13:
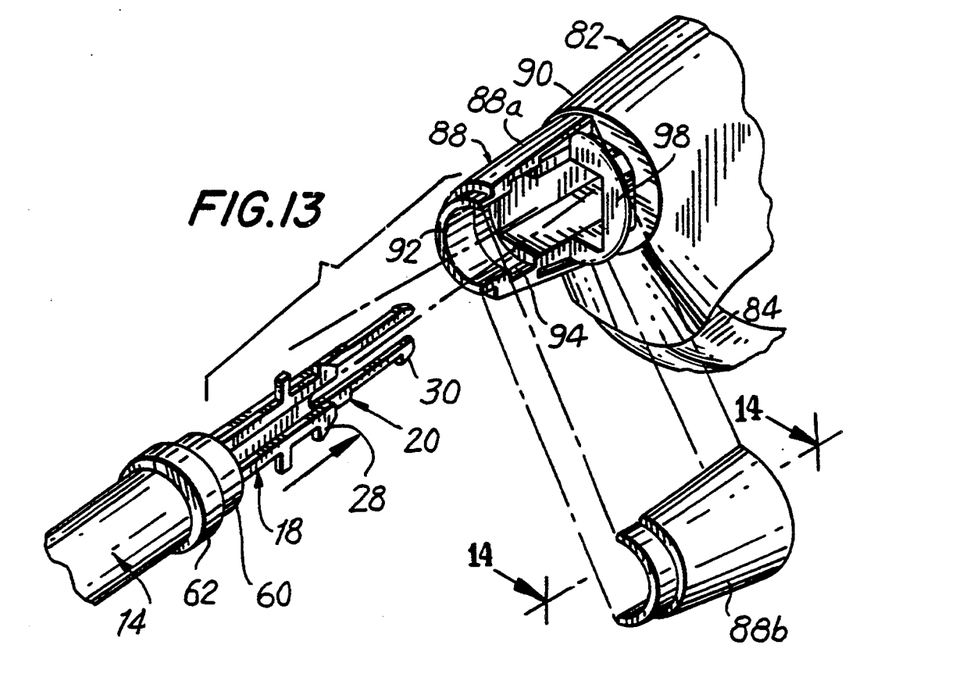
FIG. 13 is a perspective view with parts separated of a portion of the instrument of FIG. 12, illustrating an alternate embodiment for the connecting member of the present invention.
Figures 14, 15:
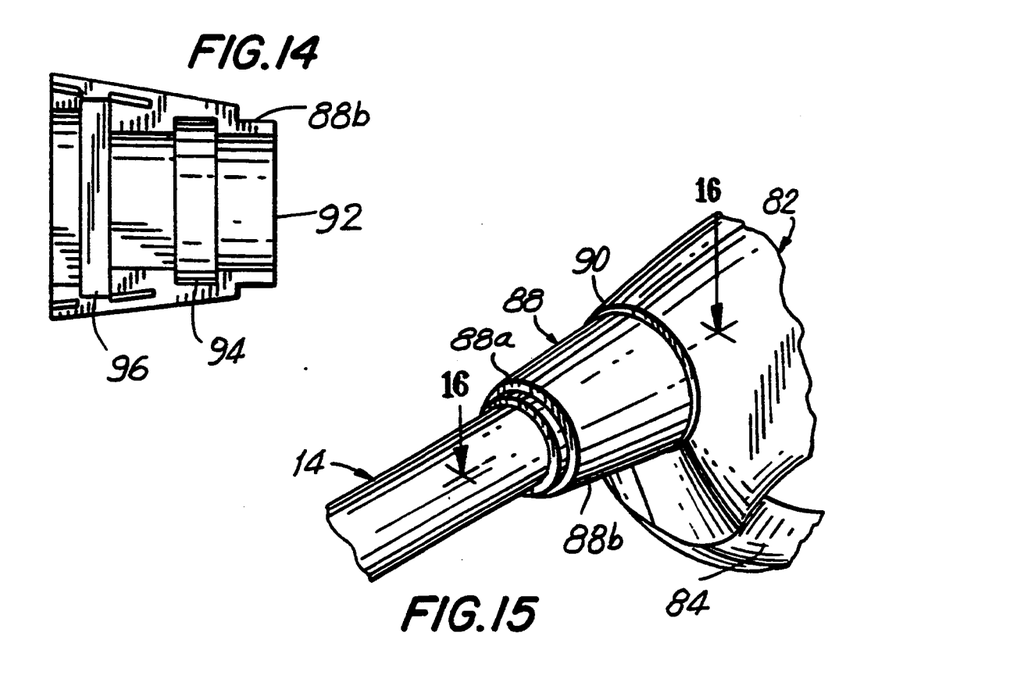
FIG. 14 is a side elevational view of a portion of the connecting member of FIG. 13.
FIG. 15 is a perspective view of a portion of the instrument of FIG. 12, illustrating the segmented connecting member of the alternate embodiment of the present invention secured about the handle assembly and the cartridge assembly.

Referring to FIGS. 13 and 14, nose 88 of handle section 82 is preferably divided into two segments 88a and 88b which comprise the connecting member for the palm grip embodiment. Nose segment 88a is formed into or secured to the distal end portion 90 of handle section 82, as shown. Nose segment 88b, shown in FIGS. 14 and 15, is substantially identical to nose section 88a, although mirror images of each other, and is separated from handle section 82. Nose 88 and distal end portion 90 of handle section 82 are provided with opening 92 which receives the proximal end portion 60 of housing 14.

Figure 16:
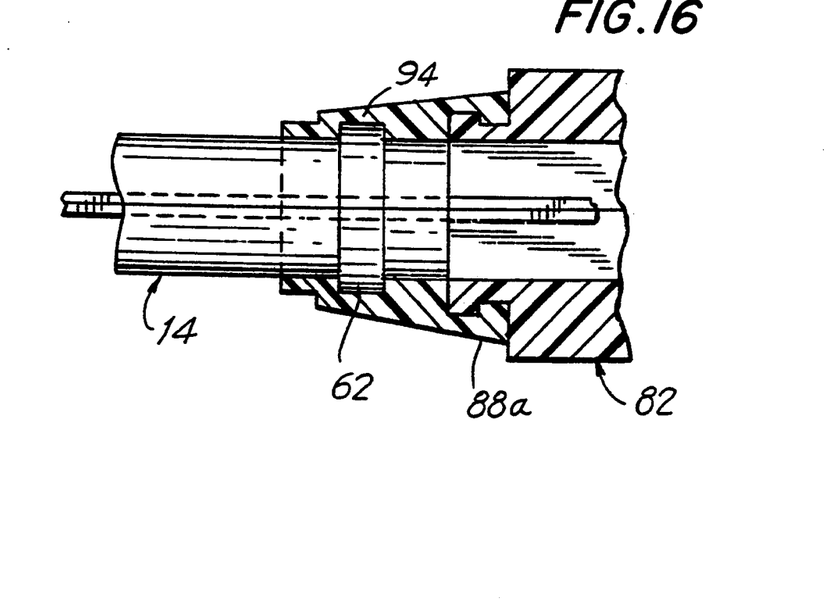
FIG. 16 is a partial cross-sectional view of a portion of the instrument of FIG. 12, taken along line 16—16 of FIG. 15.

To connect housing 14 to handle section 82, the proximal end portion 60 of housing 14 is initially inserted into opening 92 of nose 88 and handle section 82, so that the proximal end portion 28 of crimping channel 18 is operatively connected to handle 84 and the proximal end portion 30 of clip pusher 20 is operatively connected to release button 86. As previously mentioned, the operative connections between handle section 82 and housing 14 are described in U.S. Pat. No. 5,100,420. In addition to being operatively connected to handle 84 and release button 86, the proximal end portion 28 of crimping channel 18 and the proximal end portion 30 of clip pusher 20 are, preferably, arranged so as not to inhibit or limit rotational movement of the housing 14 with respect to handle section 82. In this configuration, collar 62 is positioned within channel 94 in nose segments 88a and 88b, shown in FIGS. 14 and 16. Channel 94 in combination with collar 62 secure housing 14 to handle section 82 and allow for rotational movement of housing 14 with respect to handle section 82. As noted, crimping channel 18 and clip pusher 20 are operatively connected within handle section 82 in such a manner that rotational movement of housing 14 is not interfered with.

Referring now to FIGS. 13-16, once the proximal end portion 60 of housing 14 is positioned within handle section 82, nose segment 88b is positioned about housing 14 and the distal end portion 90 of handle section 82 adjacent nose segment 88a. When positioned about nose segment 88a and housing 82, channel 96 of nose segment 88b engages support collar 98 of handle section 12. In addition, collar 62 engages channel 94 as described above. Nose segment 88b is then secured to nose segment 88a by adhesives, sonic welds or the like.

Figures 17, 18:
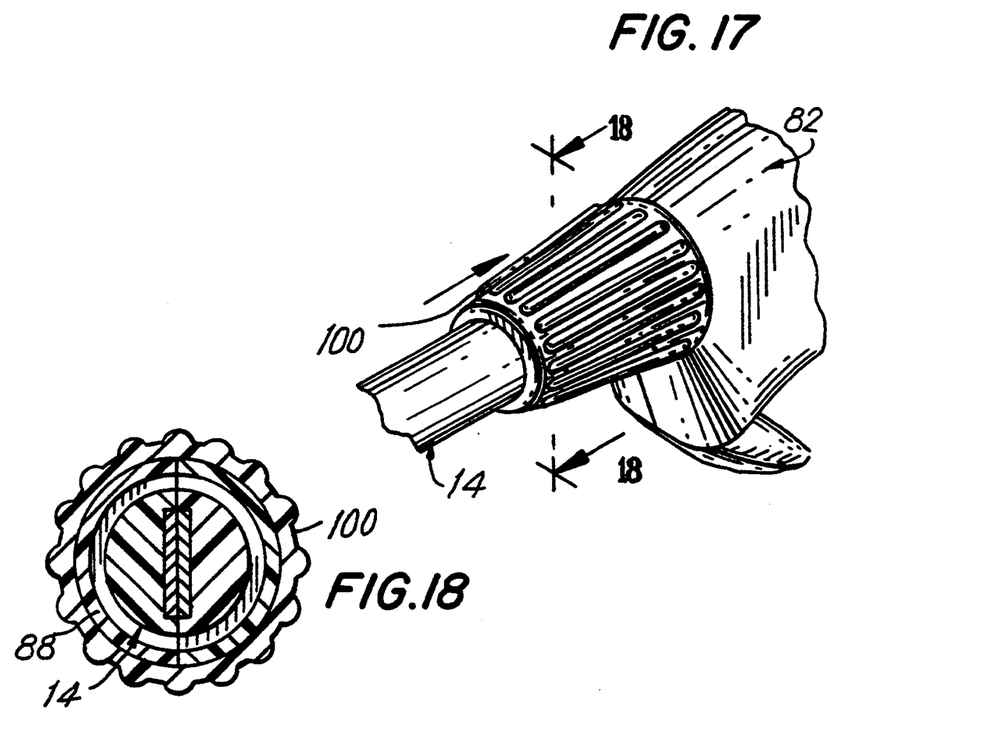
FIG. 17 is a perspective view of a portion of the instrument of FIG. 12, illustrating a rotatable collar positioned over the connecting member of the present invention.
FIG. 18 is a cross-sectional view of the surgical clip applier taken along line 18—18 of FIG. 17, illustrating the orientation of the collar about the segmented connecting member.

Referring now to FIGS. 17 and 18, rotational collar 100 may also be provided to facilitate rotational movement of housing 14. Rotational collar 100 is configured to slide along housing 14 towards nose 88 sufficiently to enclose the nose therein. The distal end of collar 100 may be secured to housing 14 by friction fit, adhesives or the like.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A surgical instrument which comprises:
   housing means having at least one active element for performing a function during surgical procedures;
   frame means having element actuating means for actuating said at least one active element, and a distal end portion adapted to receive at least a portion of said housing means; and
   connecting means associated with said frame means for releasably connecting said housing means to said frame means such that said at least one active element is operatively connected to said element actuating means and said connecting means is maintained in a fixed relationship with respect to said frame means when said housing means and said frame means are connected, and said housing means is permitted to rotate with respect to said connecting means and said frame means.

2. The surgical instrument according to claim 1, wherein said connecting means comprises a locking member adaptable for positioning about said housing means adjacent said frame means, said locking member having at least one locking tab spatially positioned at a proximal end of said locking member for engagement with a corresponding locking channel positioned at said distal end portion of said frame.

3. The surgical instrument according to claim 1, wherein said housing means includes an array of surgical fasteners.

4. The surgical instrument according to claim 3, wherein said surgical fasteners comprise surgical clips.

5. The surgical instrument according to claim 1, wherein said at least one active element includes:
jaw means positioned at a distal end of said housing means;
means for individually advancing said surgical fasteners into a position within said jaw means; and
means for closing said jaw means.

6. The surgical instrument according to claim 5, wherein said frame means includes:
fastener advancing actuating means for actuating said fastener advancing means; and
jaw closing actuating means for actuating said jaw closing means.

7. An endoscopic apparatus for releasably connecting endoscopic means to handle means such that at least a portion of said endoscopic means is removably maintained within said handle means and active elements within said endoscopic means are operatively connected to said handle means, said apparatus comprising:
a locking member adapted for positioning adjacent a proximal end of the endoscopic means and having at least one locking tab positioned at a proximal end portion of said locking member for engagement with a corresponding locking channel positioned adjacent a distal end portion of the handle means, wherein upon engagement of said locking tab with said locking channel, said locking member is maintained in a fixed relationship with respect to said handle means and said endoscopic means is permitted to rotate with respect to said locking member and said handle means.

8. A disposable apparatus for endoscopic application of surgical clips to body tissue which comprises:
a) a frame;
b) an elongated endoscopic section removably connected at the proximal end thereof to said frame and extending distally from said frame, said endoscopic section including:
i) means for storing a plurality of surgical clips;
ii) a pair of jaws positioned at the distal portion of said endoscopic section and adapted for reception of said clips;
iii) means for individually advancing said clips distally for positioning within said pair of jaws to be positioned adjacent the body tissue to be clipped;
iv) means for at least partially closing said jaws about each said clip to close said clips at least partially about the body tissue;
v) gaseous sealing means for preventing communication of gases through the apparatus; and
c) connecting means associated with said frame for removably connecting said endoscopic section to said frame and wherein said connecting means is maintained in a fixed relationship with respect to said frame when said endoscopic section and said frame are connected, and said endoscopic section is permitted to rotate with respect to said connecting means and said frame.

9. The apparatus according to claim 8, wherein said connecting means comprises a locking member rotatably, slidably positioned about said endoscopic section adjacent a proximal end thereof, said locking member having coupling means positioned at a proximal end thereof, configured, dimensioned and adapted to engage said frame such that said endoscopic section is removably connected to said frame.

10. The apparatus according to claim 9, wherein said coupling means comprises at least one tab extending proximally from said locking member.

11. The apparatus according to claim 10, wherein said at least one tab engages a corresponding keyway positioned in said frame.

12. A disposable apparatus for endoscopic application of surgical clips to body tissue which comprises:
a) a frame configured and dimensioned for manual gripping;
b) an elongated endoscopic section connected at the proximal end thereof to said frame and extending distally therefrom, said endoscopic section including:
i) means for storing a plurality of surgical clips in generally aligned relation facing the distal portion thereof;
ii) jaw means positioned at the distal end thereof and adapted for sequential reception of said clips;
iii) means for individually advancing said clips distally as to be positioned between said jaw means for positioning adjacent the body tissue to be clipped;
iv) means for selectively at least partially closing said jaw means about each said clip after the clip is advanced therebetween while simultaneously repositioning said clip advancing means for distal advancement of the next clip;
v) gaseous sealing means for preventing communication of gases through the apparatus; and
c) connecting means associated with said frame for removably connecting said endoscopic section to said frame and wherein said connecting means is maintained in a fixed relationship with respect to said frame when said endoscopic section and said frame are connected, and said endoscopic section is permitted to rotate with respect to said connecting means and said frame.

13. The apparatus according to claim 12, wherein said frame further comprises an instrument body and an actuating handle mounted to said instrument body.

14. The apparatus according to claim 12, wherein said connecting means comprises a locking member adaptable for positioning about said endoscopic section adjacent said frame, said locking member having at least one locking tab spatially positioned at a proximal end of said locking member for engagement with a corresponding locking channel positioned adjacent a distal end of said frame.

15. The apparatus according to claim 13, wherein said endoscopic section is rotatable independent of said frame.

16. The apparatus according to claim 13, wherein said jaw means comprises a pair of jaws positioned in spaced relation and configured and dimensioned for reception of a surgical clip therebetween, said pair of jaws being resiliently movable toward and away from each other in response to distal movement of said means for closing said jaw means from a proximal position to a distal position.

17. The apparatus according to claim 13 further comprising first transmission means for linearly transferring motion from said actuating handle to said clip advancing means.

18. The apparatus according to claim 13, further comprising transmission means for linearly transferring motion from said actuating handle to said jaw closing means.

19. A method for manufacturing a surgical instrument which comprises:

inserting at least a portion of a proximal end of an endoscopic housing into a corresponding opening at a distal end of a handle assembly, said opening having at least one key way positioned at least partially around the perimeter of said opening;

positioning connecting means adjacent said proximal end of said housing, said connecting means being rotatable with respect to said housing and having at least one tab positioned at proximal end thereof;

positioning said at least one tab into engagement with said at least one keyway; and rotating said connecting means such that said proximal end portion of said housing is releasably, rotatably maintained within said handle assembly.

* * * * *